United States Patent [19]

Klyce

[11] Patent Number: 5,293,533
[45] Date of Patent: Mar. 8, 1994

[54] SYSTEM FOR COMPUTERIZED FITTING OF CONTACT LENSES

[75] Inventor: Stephen D. Klyce, New Orleans, La.

[73] Assignee: Computed Anatomy, Inc., New York, N.Y.

[21] Appl. No.: 774,580

[22] Filed: Oct. 10, 1991

[51] Int. Cl.$^5$ .............................................. A61B 3/00
[52] U.S. Cl. ..................................... 351/247; 351/212
[58] Field of Search ................................. 351/212, 247

[56] References Cited

U.S. PATENT DOCUMENTS

| | | | |
|---|---|---|---|
| 4,838,682 | 6/1989 | Portnoy | 351/212 |
| 4,863,260 | 9/1989 | Gersten et al. | 351/212 |
| 5,009,498 | 4/1991 | Gersten et al. | 351/212 |
| 5,054,907 | 10/1991 | Sklar et al. | 351/212 |
| 5,110,200 | 5/1992 | Snook | 351/212 |

*Primary Examiner*—Scott J. Sugarman
*Attorney, Agent, or Firm*—Howard R. Popper

[57] ABSTRACT

A computerized system which enables the contact lens fitter to select a contact lens by specifying its "base curve" and diameter and then to obtain a visual representation of how that lens would fit the cornea of a specific patient using a simulation of the traditional fluorescein dye procedure. The patient's corneal contours are electronically stored, having been ascertained, for example, using the image scanning technique disclosed in U.S. Pat. No. 4,863,260. The contour of the contact lens is positioned to a predetermined point over the contour of the corneal surface and iteratively rotated about two axes to establish a minimum average clearance. At this point, the clearance is depicted by a color display analogous to that which would be obtained using the actual contact lens on the patient's cornea with the fluorescein dye.

11 Claims, 7 Drawing Sheets

(3 of 7 Drawing(s) in Color)

SYSTEM FOR COMPUTERIZED FITTING OF CONTACT LENSES

TECHNICAL FIELD

This invention relates to computerized medical diagnostic instrumentation and, more particularly, to a system for fitting contact lenses.

BACKGROUND ART

Contact lenses that ride directly over the corneal surface of the eye, floating on a micro-thin layer of tear fluid, are widely prescribed to correct refractive errors in vision. However, the traditional method of fitting contact lenses is a laborious process, often requiring weeks of trying various lens shapes. Each fitting usually requires at least fifteen minutes before the patient is comfortable with the lens in place. Then the optometrist applies fluorescein dye drops to the patient's eye to reveal the amount of clearance between the contact lens and the corneal surface. Fluorescein is a bright orange dye that fluoresces lime green in the presence of cobalt blue light. It is relatively harmless although an occasional person may have an allergic response. In the lens fitting process, the more clearance between the contact lens and the cornea, the more dye is permitted in the space, as indicated by a fuller green fluorescence of the dye. The fluorescein test is considered quite reliable but is not usable with the popular soft contact lenses because the material from which they are made, hydrogel, absorbs the fluorescein dye, staining the lens. It would be useful to provide a method of fitting contact lenses which avoids the need to test multiple contact lenses in the patient's eye.

SUMMARY OF THE INVENTION

In accordance with the principles of the present invention, in one illustrative embodiment thereof, the fitting of contact lenses employs a computerized image of the patient's cornea, advantageously obtained with the apparatus disclosed in U.S. Pat. No. 4,863,260. The contour of the contact lens is electronically specified and stored in the computer and then positioned at a predetermined point over the electronically stored contour of the corneal surface. The contact lens contour is then iteratively rotated about two axes to establish a minimum average clearance. The clearance is depicted by a color display analogous to that which would be obtained using the actual contact lens on the patient's cornea with the fluorescein dye.

BRIEF DESCRIPTION OF THE DRAWINGS

The file of this patent contains at least one drawing executed in color. Copies of this patent with color drawing(s) will be provided by the Patent and Trademark Office upon a request and payment of the necessary fee.

The foregoing objects and features of the invention may become more apparent after a consideration of the drawings, in consideration with the general description below.

DETAILED DESCRIPTION

Figure 1:
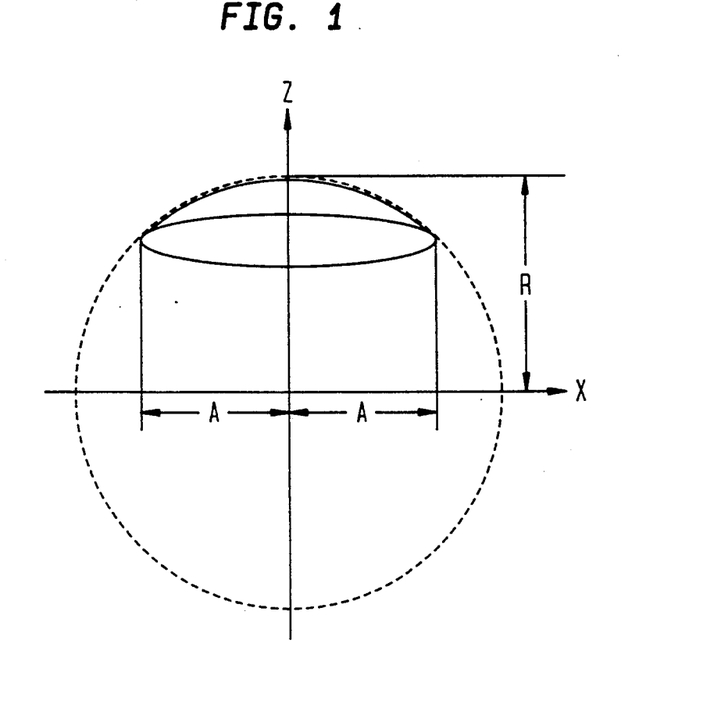
FIG. 1 shows the relationship between contact lens diameter, and base curvature which specify a specific contact lens to the system of my invention.
Figure 2:
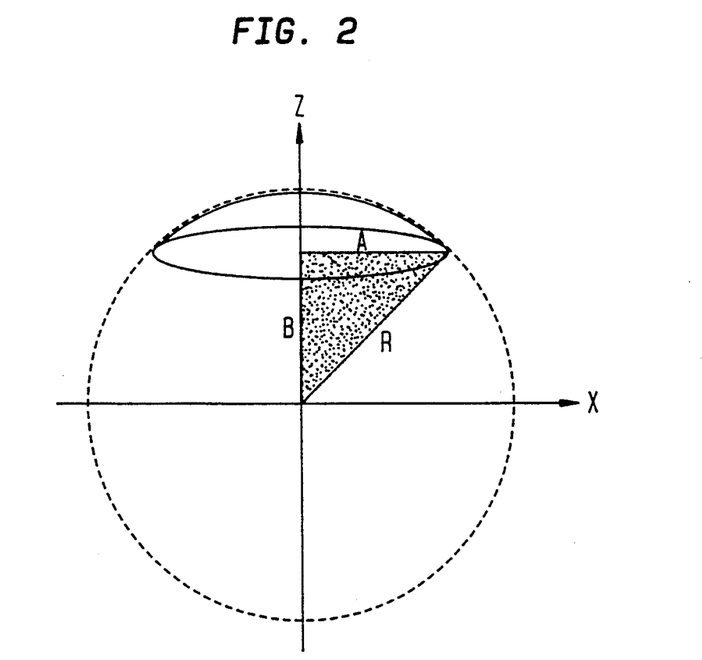
FIG. 2 shows how lens "offset" is defined, i.e., the distance "B" from the center of a sphere having the same radius of curvature as the lens to the plane which includes the base diameter (equal to "2A") of the contact lens.

Referring to FIG. 1, the dimension labeled r, is the base curvature of the contact lens under consideration and is the radius of a hypothetical sphere which contains the base of the contact lens. The diameter, 2A, of the base of the lens and its base curvature, r, are input by the system user to specify the particular contact lens under consideration. FIG. 2 shows the "offset", dimension "B", which is the distance from the center of a sphere having the same radius of curvature as the lens to the plane which includes the base diameter, 2A, of the contact lens.

Figure 3:
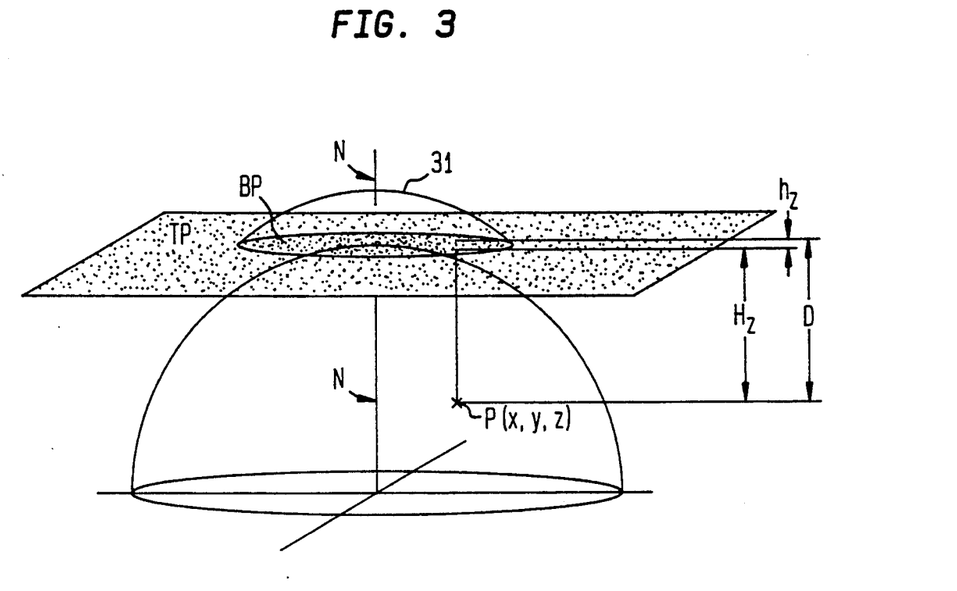
FIG. 3 shows the distance, D, between a point on the surface of the patient's cornea and a point on the (under) surface of a contact lens for a first position assumed in the process of my invention.

Referring to FIG. 3, the contour representing the contact lens 31 is positioned so that its base diameter lies in a plane which is initially tangent to the apical normal N of the contour representing the patient's cornea. When correctly fit, the radius of curvature of the contact lens will approach the radius of curvature of the contour representing the cornea. The exact contour required is a matter of professional judgement. The purpose of my invention is to guide the exercise of that judgment. Accordingly, we may, for the purpose of simplifying the drawing depict the cornea as being generally spherical.

It will be recalled that the prior art Gersten et al. U.S. Pat. No. 4,863,260 obtained its measurements of the corneal surface by accurately positioning the corneal apex at a predetermined point defined by a pair of intersecting laser beams. In FIG. 3, plane TP is the plane defined by that predetermined point and the distance $H_z$ measured in the z-axis direction between any point $p_{(x,y,z)}$ on the corneal surface and the tangent plane TP passing through the corneal apex is provided by the '260 patent. The height $h_z$ of any point on contact lens 31 is measured in the z-axis direction from its base plane BP and is provided by calculation from the specified geometry of the lens once the base curve and diameter defining the contact lens have been specified.

The equation for the three dimensional coordinates of any point on the surface of a sphere whose center is at coordinates a, b, c is:

$$r^2 = (x-a)^2 + (y-b)^2 + (z-c)^2, \quad (1)$$

where r=spherical radius. If the sphere's center is at a=0, b=0, c=0, the equation for the surface of the sphere is simply:

$$r^2 = x^2 + y^2 + z^2, \quad (2)$$

The distance D measured in the z-axis direction between the point $p_{(x,y,z)}$ on the corneal surface and the corresponding point (at the same x, y coordinates) on the under surface of contact lens 31 is given by $$D = H_z + h_z \quad (3)$$

Figure 4:
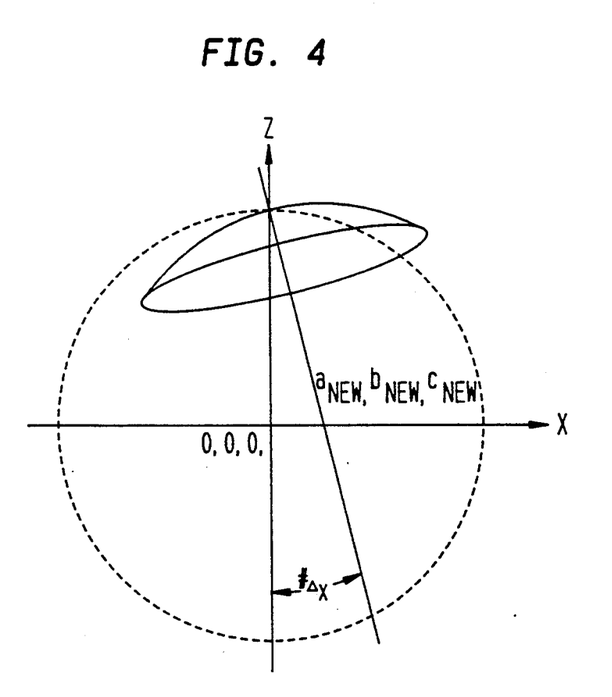
FIG. 4 shows the rotation of a contact lens about the y-axis which is assumed to be perpendicular to the plane of the paper.

In accordance with one aspect of my invention it is desired to minimize the *average* clearance between the lens and the sphere. The next step in the method is to "lower" the lens onto the sphere and then to rotate the lens first about one axis, as depicted in FIG. 4, until a minimum average clearance is found. Then, holding constant along that axis, rotate the lens about the other axis until a minimum average clearance is again found. Holding constant on this axis, the lens is again rotated on the first axis of rotation, and so on until the true minimal average clearance is calculated.

The minimum average clearance is found after recalculating the new heights under the rotated lens. The new heights are found by solving for the coordinates of the center of rotation $a_{new}$ and $b_{new}$ then, using these values to find $c_{new}$. With the new heights, the average clearance can be recalculated. The relevant equations are as follows:

$$a_{new} = r \sin(\theta_{\Delta x}), \quad (4)$$

$$b_{new} = r \sin(\theta_{\Delta y}), \text{ and} \quad (5)$$

$$c_{new} = \sqrt{r^2 - a_{new}^2 - b_{new}^2} - r. \quad (6)$$

One last consideration when calculating minimum average clearance is the effect and control of experimental noise. Noise can be categorized in many ways, such as white noise, and is always a concern to an inventor. An inventor usually seeks to boost a quantity know as the signal-to-noise ratio. In this invention, noise is controlled by rotating an axis further than necessary to determine minima to look for further minima. If none are found, than the apparent minimum is real. Else the invention continues to search for new minimum and test for noise.

Figure 5:
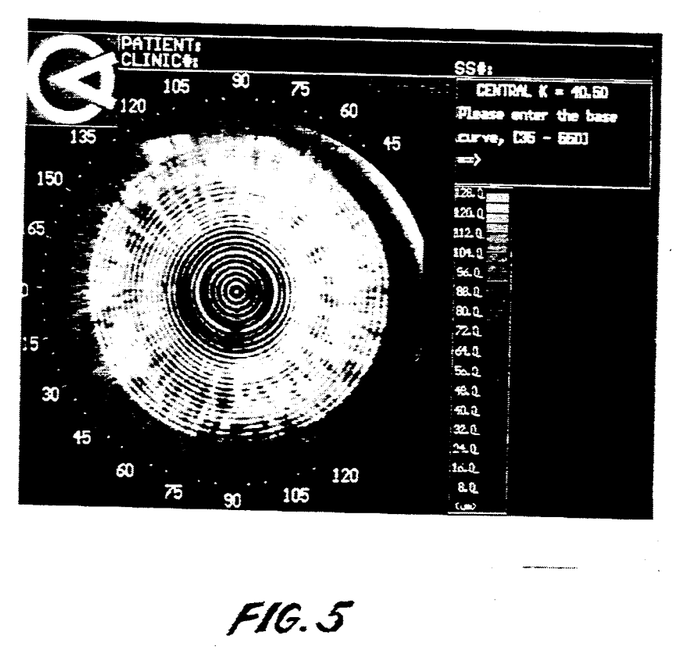
FIG. 5 is a photograph of the video image of a patient's cornea showing the pattern of structured light used to provide the basis for the topographic description of the cornea.

Finally, all data and calculations are plotted graphically. The output appears on a color video screen and, if desired, can be permanently recorded using a video recorder. First, a picture of the raw data appears on the screen. See FIG. 5. This is the actual image of the eye as obtained by the video camera. In addition, statistics appear on the screen such as the patient's name, social security number, etc.; the clinic's identification number, etc.; polar coordinates arranged appropriately about the picture of the eye; a micrometer color scale; and the simulated keratometry data which can be used as the starting point for the lens fitter fitting an actual contact lens. When the lens curvature is input, another question asks for the desired lens diameter. When the diameter is input, the apparatus has all it needs to calculate the average clearance and provide graphical mimicry of the fluorescein dye test, the main objectives behind this invention.

Figure 6:
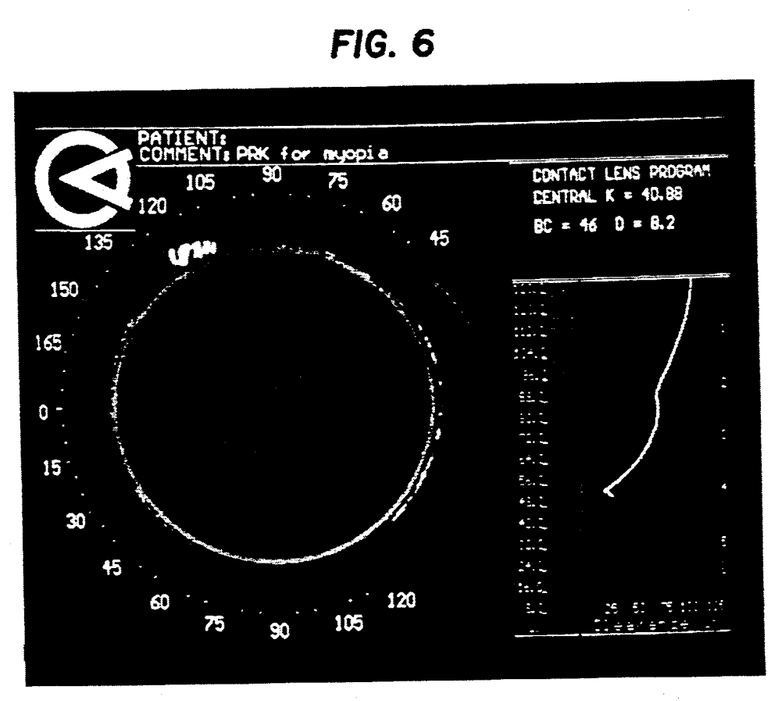
FIG. 6 is a photograph of the image presented by my invention simulating the use of a fluorescein dye to illustrate the clearance between a selected contact lens and the patient's cornea.
Figure 7:
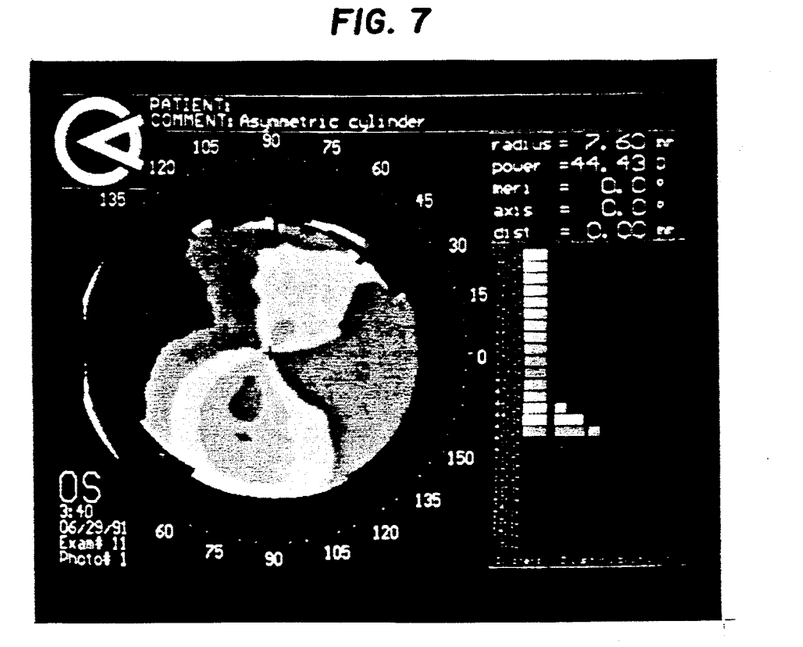
FIG. 7 is a photograph of the topography of a patient's cornea provided by the apparatus disclosed in U.S. Pat. No. 4,863,260.
Figure 8:
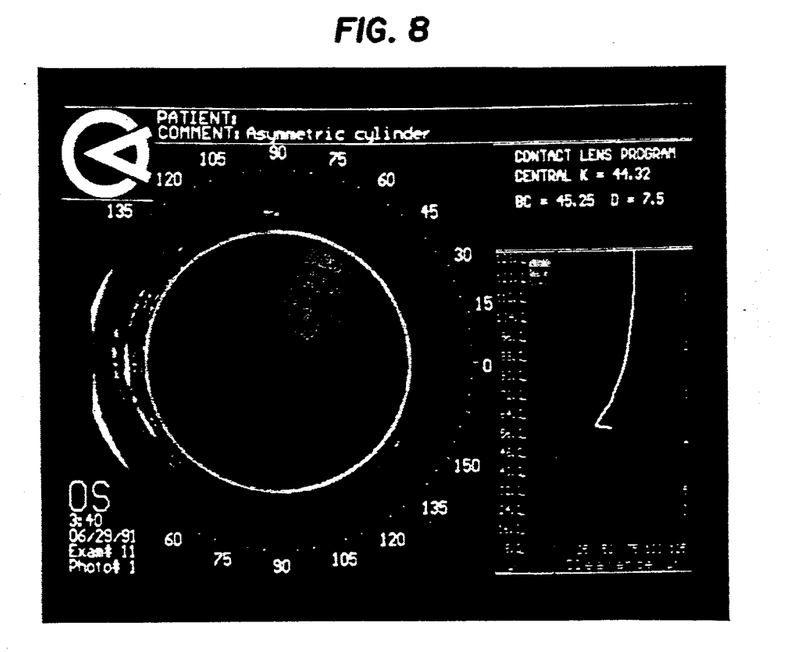
FIG. 8 is a photograph of the fitting of a contact lens to the cornea of FIG. 7 employing the apparatus of my invention.
Figure 9:
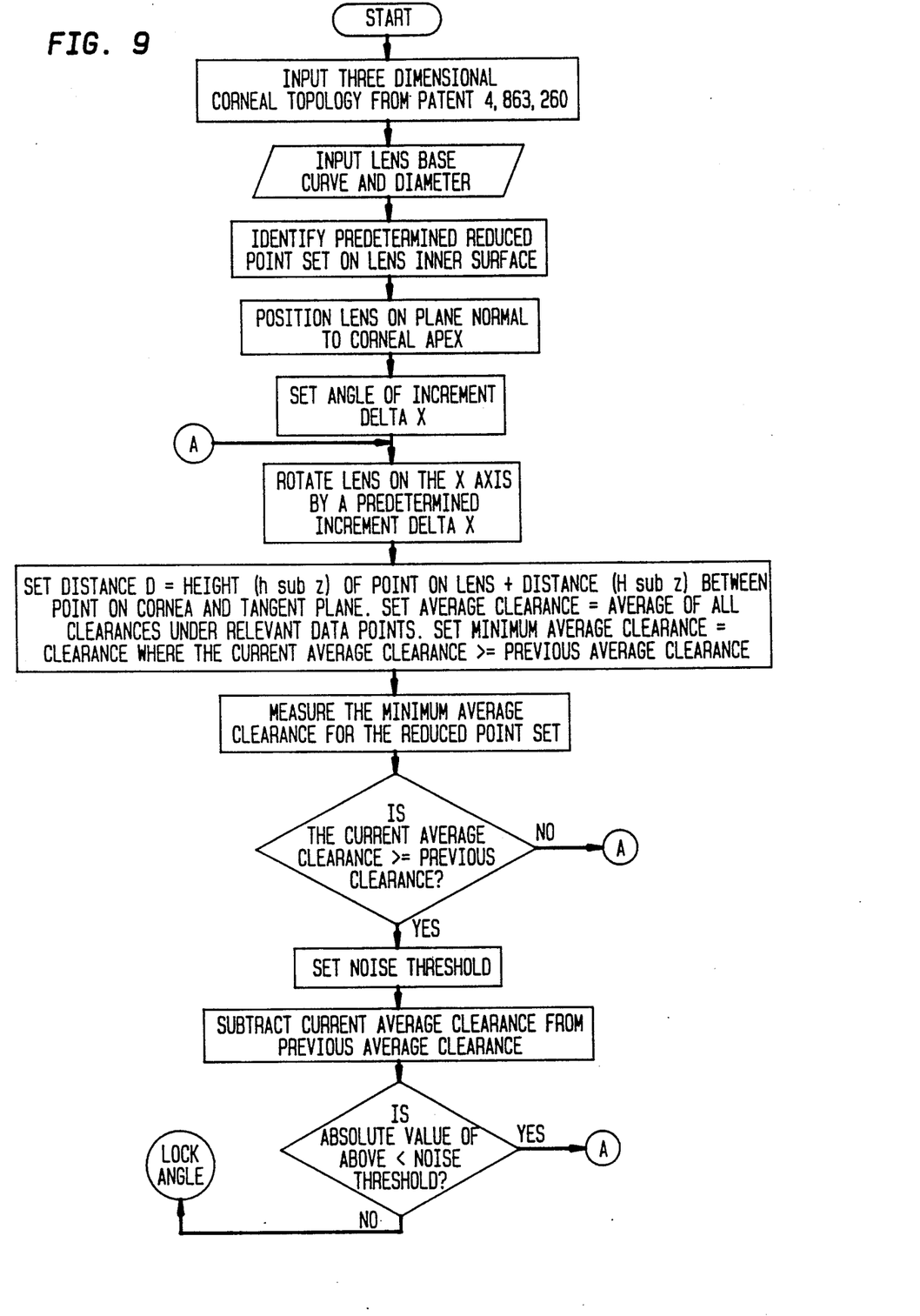
FIGS. 9 and 10 are a flow chart of the computer processing steps performed in accordance with my invention.
Figure 10:
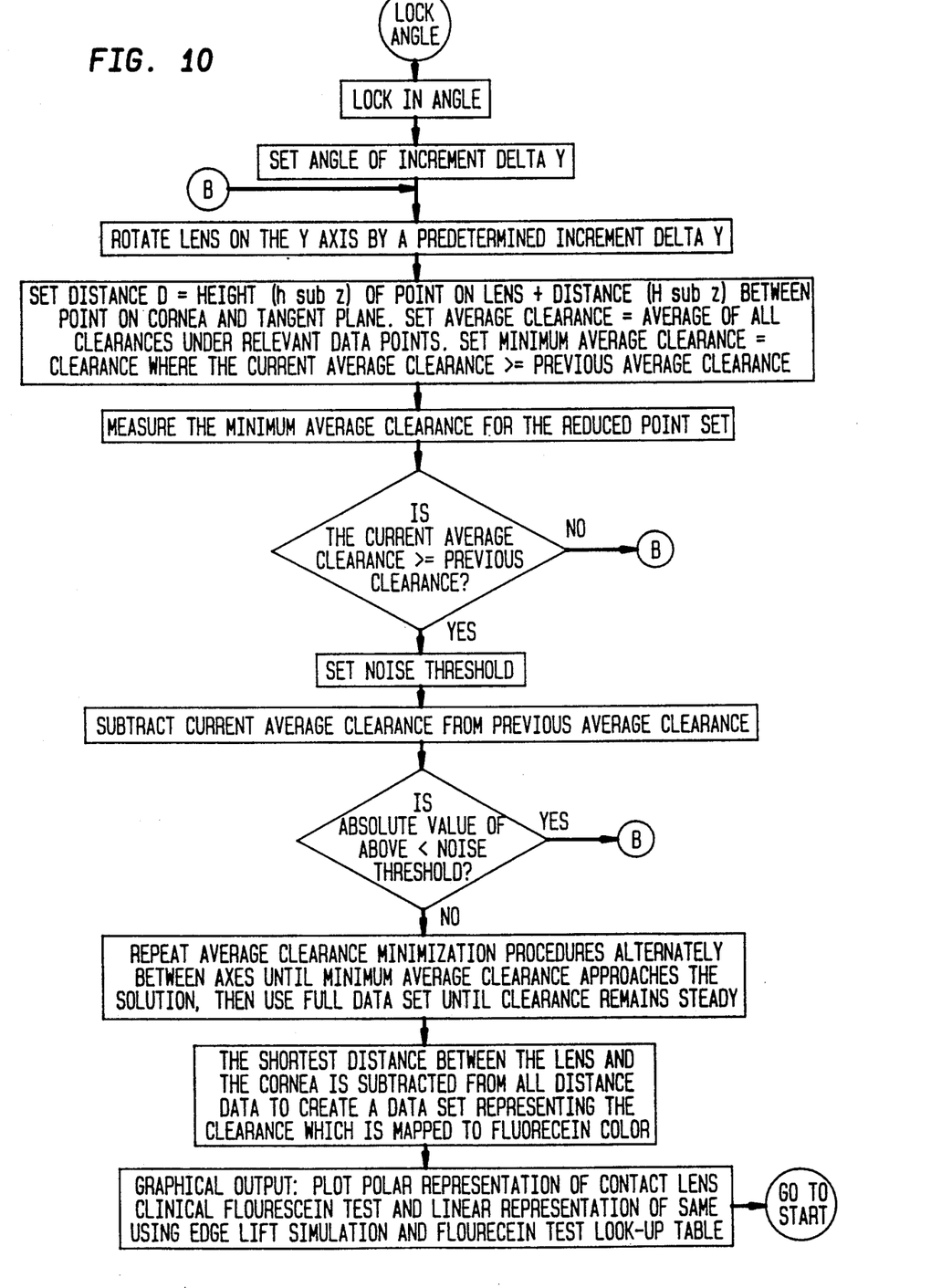

The video output of the computer-mimicked fluorescein dye test consists of an overlay of graphical features upon the pre-existing screen of the raw data. See FIG. 6. All output remains as before except the following: the question box becomes a data box, echoing the input lens curvature and diameter; the empty box to the right of the color scale fills with a line graph of the average clearance in micrometers versus the distance in millimeters from the center of the contact lens; and the eye itself is covered with a graphical color-scaled representation of the calculated appearance of the fluorescein dye test. The line graph and the color-scaled view both represent the presentation of the same data, except the line graph presents an average of all meridians while the color map presents the data in all meridians.

The color map is presented so as to mimic the fluorescein test as closely as possible. Recall that the fluorescein test consists of the placing into the eye a dye which visually relates information regarding the clearance. Fluorescein, a bright orange dye that fluoresces lime green under cobalt blue light, will fluoresce more brightly green where there is more clearance, and will not appear at all where there is little or no clearance. Instead, the subject will appear cobalt blue where there is little clearance. The relationship between the presence of fluorescein and its fluorescent intensity is not linear, however, and must be taken into account. The fluorescence will not increase at all beyond a certain distance nor is it discernable visually until a certain concentration is present. The invention takes account of both of these effects through the medium of a look-up table for corresponding fluorescence brightness values and clearances. The invention finds the clearance then reports the fluorescent brightness value for that point. This is repeated for all the thousands of data points.

One final consideration is the edge lift of the contact lens. Each manufacturer has a proprietary method by which the contact lens is trimmed on the inside edge around the base. The trimming is necessary to provide comfort, safety, and for other reasons. As a result of this edge lift, the clinical fluorescein test would reveal a bright green ring around the entire lens. Although specifically asked, no manufacturer has been willing to reveal data on their edge lift techniques. Thus this invention must simulate the edge lift phenomenon. Edge lift has been simulated and will be directly accounted for once manufacturers are willing to provide data.

What is claimed is:

1. The process of automating the selection of an ocular contact lens to fit a patient's eye using a computer simulation of the fluorescein dye test, comprising the steps of:
   a. reading data defining the corneal topography of the patient whose eye is to receive the contact lens;
   b. reading data defining the interior surface topography of a contact lens;
   c. determining the minimum average clearance between the topography of the contact lens and the cornea; and
   d. displaying said clearance using the same degree of fluorescence and fluorescent intensity corresponding to that which would be exhibited by fluorescein dye contained in a space equal to said minimum average clearance.

2. The process of claim 1 wherein said displaying of said fluorescein dye appears bright lime green in areas of maximum clearance and dark cobalt blue in areas of no clearance.

3. The process of claim 1 wherein said display includes a line graph of the minimum average clearance versus the distance of the contact lens from the center of the lens to its edge.

4. The process of claim 1 wherein said display includes echoing a dioptric color map of corneal topography.

5. The process of claim 1 wherein said display includes echoing the base curve and diameter parameters of said contact lens.

6. The process of claim 1 wherein said display includes a display of the edge lift of a lens by simulating the appearance of an increased amount of fluorescein dye in the area of such edge lift.

7. The process of claim 1 wherein said display simulates the nonlinear brightness and hue response of fluorescein dye to said clearance.

8. The process of automating the selection of an ocular contact lens to fit a patient's eye using a computer simulation of the fluorescein dye test, comprising the steps of:
   a. using stored data to simulate the positioning of a contact lens on a tangent plane normal to the apex of the cornea of the patient whose eye is to receive the contact lens;
   b. determining the height of a point on the surface of the contact lens from the plane of the base of said lens;
   c. determining the height of a corresponding point on the surface of the cornea to said tangent plane;
   d. determining the distance between said corresponding points;
   e. simulating the lowering of the lens onto corneal surface until such surfaces touch at at least one point;
   f. iteratively rotating said contact lens about two axes until an apparent minimum average clearance is achieved; and
   g. further rotating said contact lens to determine if said apparent minimum exceeds a predetermined increase corresponding to background noise.

9. The process of claim 8 comprising the step of:
   a. displaying said minimum average clearance using the same degree of fluorescence and fluorescent intensity corresponding to that which would be exhibited by fluorescein dye contained in a space equal to said minimum average clearance.

10. The process of claim 8 wherein a sparse set of points defining the topography of said corneal and contact lens surfaces is preliminarily used to establish a first said minimum average clearance determined by the existence of any bumps on the corneal surface followed thereafter by employing a full data set of surface points to determine a final said minimum average clearance.

11. The process of claim 8 wherein large changes in angles of axis rotation are preliminarily used to establish a first said minimum average clearance until the solution is overshot, then reversing the direction of change in angle using smaller changes.

* * * * *